US012626809B2

(12) United States Patent
Mattmiller et al.

(10) Patent No.: US 12,626,809 B2
(45) Date of Patent: May 12, 2026

(54) INVENTORY SYSTEMS AND METHODS FOR DETECTING AND COUNTING POTENTIALLY RETAINED SURGICAL ITEMS

(71) Applicant: Covidien LP, Mansfield, MA (US)

(72) Inventors: Aaron G. Mattmiller, Berthoud, CO (US); Joel R. Helgerson, Erie, CO (US); Edward L. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 760 days.

(21) Appl. No.: 17/859,530

(22) Filed: Jul. 7, 2022

(65) Prior Publication Data

US 2023/0041495 A1 Feb. 9, 2023

Related U.S. Application Data

(60) Provisional application No. 63/230,984, filed on Aug. 9, 2021.

(51) Int. Cl.
G16H 40/20 (2018.01)
G06K 19/077 (2006.01)

(52) U.S. Cl.
CPC ....... G16H 40/20 (2018.01); G06K 19/07722 (2013.01); G06K 19/07773 (2013.01)

(58) Field of Classification Search
CPC ............. G16H 40/20; G06K 19/07722; G06K 19/07773; A61B 2090/0803; A61B 90/98;
(Continued)

(56) References Cited

U.S. PATENT DOCUMENTS 2,740,405 A 4/1956 Riordan
3,422,816 A 1/1969 Robinson et al.
(Continued)

FOREIGN PATENT DOCUMENTS

AU 2003249257 A1 2/2004
CN 105373826 A 3/2016
(Continued)

OTHER PUBLICATIONS

Kranzfelder, Real-Time Monitoring for Detection of Retained Surgical Sponges and Team Motion in the Surgical Operation Room Using Radio-Frequency-Identification (RFID) Technology: A Preclinical Evaluation, 2012, Journal of Surgical Research, vol. 175, Issue 2, pp. 191-198 (Year: 2012).*
(Continued)

*Primary Examiner* — David J Stoltenberg
*Assistant Examiner* — Tran N Nguyen
(74) *Attorney, Agent, or Firm* — Carter, DeLuca & Farrell, LLP

(57) ABSTRACT
An inventory system configured for detecting and counting potentially retained surgical items within a body of a patient includes a dual detection tag, a signal generator, and an antenna operably coupled to the signal generator. The dual detection tag includes a beacon tag configured to transmit a first return signal at a first frequency when energized and a RFID tag affixed configured to transmit a second return signal at a second frequency when energized. The signal generator is configured to generate an energizing signal for the beacon tag and/or the RFID tag. The antenna configured to receive the first return signal transmitted by at least one of the beacon tag or the second return signal transmitted by the RFID tag.

18 Claims, 6 Drawing Sheets

(58) Field of Classification Search
CPC ........... A61B 90/08; A61B 2090/0804; A61B
2090/0805
See application file for complete search history.

(56) References Cited

U.S. PATENT DOCUMENTS

| | | | |
|---|---|---|---|
| 3,587,583 A | 6/1971 | Greenberg | |
| 4,114,601 A | 9/1978 | Abels | |
| 4,193,405 A | 3/1980 | Abels | |
| 4,422,548 A | 12/1983 | Cheesman et al. | |
| 4,658,818 A | 4/1987 | Miller, Jr. et al. | |
| 4,681,111 A | 7/1987 | Silvian | |
| 4,893,118 A | 1/1990 | Lewiner et al. | |
| 5,031,642 A | 7/1991 | Nosek | |
| 5,057,095 A | 10/1991 | Fabian | |
| 5,105,829 A | 4/1992 | Fabian et al. | |
| 5,107,862 A | 4/1992 | Fabian et al. | |
| 5,188,126 A | 2/1993 | Fabian et al. | |
| 5,190,059 A | 3/1993 | Fabian et al. | |
| 5,235,326 A | 8/1993 | Beigel et al. | |
| 5,258,742 A | 11/1993 | Soldevila Domingo et al. | |
| 5,329,944 A | 7/1994 | Fabian et al. | |
| 5,353,011 A | 10/1994 | Wheeler et al. | |
| 5,446,447 A | 8/1995 | Carney et al. | |
| 5,456,718 A | 10/1995 | Szymaitis | |
| 5,482,036 A | 1/1996 | Diab et al. | |
| 5,629,498 A | 5/1997 | Pollock et al. | |
| 5,650,596 A | 7/1997 | Morris et al. | |
| 5,664,582 A | 9/1997 | Szymaitis | |
| 5,886,672 A | 3/1999 | Brune et al. | |
| 5,923,001 A | 7/1999 | Morris et al. | |
| 5,928,151 A | 7/1999 | Hossack et al. | |
| 6,026,818 A | 2/2000 | Blair et al. | |
| 6,211,666 B1 | 4/2001 | Acker | |
| 6,215,437 B1 | 4/2001 | Schurmann et al. | |
| 6,223,137 B1 | 4/2001 | McCay et al. | |
| 6,232,878 B1 | 5/2001 | Rubin | |
| 6,270,460 B1 | 8/2001 | McCartan et al. | |
| 6,349,234 B2 | 2/2002 | Pauly et al. | |
| 6,359,562 B2 | 3/2002 | Rubin | |
| 6,366,206 B1 | 4/2002 | Ishikawa et al. | |
| 6,401,722 B1 | 6/2002 | Krag | |
| 6,557,752 B1 | 5/2003 | Yacoob | |
| 6,588,661 B2 | 7/2003 | Degrauwe et al. | |
| 6,632,216 B2 | 10/2003 | Houzego et al. | |
| 6,633,226 B1 | 10/2003 | Nysen | |
| 6,641,039 B2 | 11/2003 | Southard | |
| 6,648,223 B2 | 11/2003 | Boukhny et al. | |
| 6,650,240 B2 | 11/2003 | Lee et al. | |
| 6,696,954 B2 | 2/2004 | Chung | |
| 6,734,795 B2 | 5/2004 | Price | |
| 6,777,623 B2 * | 8/2004 | Ballard | G01G 23/3728 |
| | | | 705/28 |
| 6,786,405 B2 | 9/2004 | Wiedenhoefer | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,861,954 B2 | 3/2005 | Levin | |
| 6,879,300 B2 | 4/2005 | Rochelle et al. | |
| 6,909,366 B1 | 6/2005 | Marsh et al. | |
| 6,977,504 B2 | 12/2005 | Wright et al. | |
| 6,998,541 B2 | 2/2006 | Morris et al. | |
| 7,001,366 B2 | 2/2006 | Ballard | |
| 7,019,650 B2 | 3/2006 | Volpi et al. | |
| 7,026,924 B2 | 4/2006 | Degrauwe et al. | |
| 7,026,927 B2 | 4/2006 | Wright et al. | |
| 7,098,793 B2 | 8/2006 | Chung | |
| 7,098,866 B2 | 8/2006 | Desjeux et al. | |
| 7,135,978 B2 | 11/2006 | Gisselberg et al. | |
| 7,142,815 B2 | 11/2006 | Desjeux et al. | |
| 7,158,030 B2 | 1/2007 | Chung | |
| 7,158,754 B2 | 1/2007 | Anderson | |
| 7,160,258 B2 | 1/2007 | Imran et al. | |
| 7,176,798 B2 | 2/2007 | Dimmer et al. | |
| 7,256,695 B2 | 8/2007 | Hamel et al. | |

| | | | |
|---|---|---|---|
| 7,256,696 B2 | 8/2007 | Levin | |
| 7,268,684 B2 | 9/2007 | Tethrake et al. | |
| 7,299,981 B2 | 11/2007 | Hickle et al. | |
| 7,319,396 B2 | 1/2008 | Homanfar et al. | |
| 7,319,397 B2 | 1/2008 | Chung et al. | |
| 7,325,723 B2 | 2/2008 | Desjeux | |
| 7,342,497 B2 | 3/2008 | Chung et al. | |
| 7,362,228 B2 | 4/2008 | Nycz et al. | |
| 7,382,255 B2 | 6/2008 | Chung | |
| 7,397,364 B2 | 7/2008 | Govari | |
| D577,421 S | 9/2008 | Williams | |
| 7,420,468 B2 | 9/2008 | Fabian et al. | |
| 7,423,535 B2 | 9/2008 | Chung et al. | |
| 7,464,713 B2 | 12/2008 | Fabian et al. | |
| 7,492,257 B2 | 2/2009 | Tethrake et al. | |
| 7,508,303 B2 | 3/2009 | Capowski et al. | |
| 7,513,425 B2 | 4/2009 | Chung | |
| 8,111,162 B2 | 2/2012 | Barnes et al. | |
| 8,358,212 B2 | 1/2013 | Blair | |
| 2001/0030610 A1 | 10/2001 | Rochelle et al. | |
| 2002/0032435 A1 | 3/2002 | Levin | |
| 2002/0143320 A1 | 10/2002 | Levin | |
| 2002/0188259 A1 | 12/2002 | Hickle et al. | |
| 2003/0004411 A1 | 1/2003 | Govari et al. | |
| 2003/0052788 A1 | 3/2003 | Kwong-Tai Chung | |
| 2003/0105394 A1 | 6/2003 | Fabian et al. | |
| 2003/0111592 A1 | 6/2003 | Al-Ali | |
| 2004/0008123 A1 | 1/2004 | Carrender et al. | |
| 2004/0129279 A1 | 7/2004 | Fabian et al. | |
| 2004/0137844 A1 | 7/2004 | Desjeux et al. | |
| 2004/0250819 A1 | 12/2004 | Blair et al. | |
| 2005/0049564 A1 | 3/2005 | Fabian | |
| 2005/0110640 A1 | 5/2005 | Chung | |
| 2006/0106368 A1 | 5/2006 | Miller et al. | |
| 2006/0187044 A1 | 8/2006 | Fabian et al. | |
| 2006/0202827 A1 | 9/2006 | Volpi et al. | |
| 2006/0202835 A1 | 9/2006 | Thibault | |
| 2006/0235488 A1 | 10/2006 | Nycz et al. | |
| 2006/0241396 A1 * | 10/2006 | Fabian | A61B 5/06 |
| | | | 340/572.1 |
| 2006/0241399 A1 | 10/2006 | Fabian | |
| 2007/0004994 A1 | 1/2007 | Sherman | |
| 2007/0005141 A1 | 1/2007 | Sherman | |
| 2007/0239289 A1 | 10/2007 | Cambre et al. | |
| 2007/0265690 A1 | 11/2007 | Lichtenstein et al. | |
| 2007/0285249 A1 | 12/2007 | Blair et al. | |
| 2008/0007411 A1 | 1/2008 | Levin | |
| 2008/0051746 A1 | 2/2008 | Shen-Gunther | |
| 2008/0132860 A1 | 6/2008 | Smith et al. | |
| 2008/0204245 A1 | 8/2008 | Blair et al. | |
| 2008/0231452 A1 | 9/2008 | Levin | |
| 2008/0237341 A1 | 10/2008 | Fleck et al. | |
| 2008/0238677 A1 | 10/2008 | Blair et al. | |
| 2008/0272913 A1 | 11/2008 | Barnes et al. | |
| 2008/0281190 A1 | 11/2008 | Petcavich et al. | |
| 2008/0296373 A1 | 12/2008 | Zmood et al. | |
| 2011/0174877 A1 | 7/2011 | Fleck et al. | |
| 2011/0230147 A1 | 9/2011 | Schuh et al. | |
| 2013/0201005 A1 * | 8/2013 | Stevenson | B60R 25/00 |
| | | | 340/10.1 |
| 2014/0273865 A1 | 9/2014 | Skarda et al. | |
| 2016/0055359 A1 * | 2/2016 | Jensen | A61B 90/98 |
| | | | 340/10.5 |
| 2016/0206399 A1 * | 7/2016 | Blair | A61B 34/20 |
| 2017/0258551 A1 * | 9/2017 | Smith | G16H 40/20 |
| 2020/0030039 A1 | 1/2020 | Yavari et al. | |

FOREIGN PATENT DOCUMENTS

| | | | |
|---|---|---|---|
| EP | 1612554 A1 | 1/2006 | |
| KR | 2018/0130784 A | 12/2018 | |
| WO | 2004008387 A1 | 1/2004 | |
| WO | 2004086997 A1 | 10/2004 | |
| WO | 2006060781 A1 | 6/2006 | |
| WO | 2006091765 A2 | 8/2006 | |
| WO | 2016086168 A1 | 6/2016 | |

(56) References Cited

OTHER PUBLICATIONS

Kranzfelder, Real-Time Monitoring for Detection of Retained Surgical Sponges and Team Motion in the Surgical Operation Room Using Radio-Frequency-Identification (RFID) Technology: A Preclinical Evaluation, Journal of Surgical Research, vol. 175, Issue 2, pp. 191-198 (Year: 2012).*

Parlak, Introducing RFID technology in dynamic and time-critical medical settings: Requirements and challenges, Journal of Biomedical Informatics 45 (2012) 958-974 (Year: 2012).*

Bolotnyy, The Case for Multi-Tag RFID Systems, International Conference on Wireless Algorithms, Systems and Applications (WASA 2007), Chicago, IL, USA, pp. 174-186 (Year: 2007).*

Bolotnyy, Multi-Tag RFID Systems, International Journal of Internet Protocol Technology (IJIPT), special issue on RFID: Technologies, Applications, and Trends (Year: 2007).*

Extended European Search Report dated Jan. 2, 2023 corresponding to counterpart Patent Application EP 22189319.1.

Barnes et al., "Design for a FET Based 1 MHZ, 10kV Pulse Generator," Pulsed Power Conference, Digest of Technical Papers, Tenth IEEE International, 2:1335-1340, 1995.

Macario et al., "Initial Clinical Evaluation of a Handheld Device for Detecting Retained Surgical Gauze Sponges Using Radiofrequency Identification Technology," Arch. Surg., vol. 14, Jul. 2005, pp. 659-662.

* cited by examiner

100

500

INVENTORY SYSTEMS AND METHODS FOR DETECTING AND COUNTING POTENTIALLY RETAINED SURGICAL ITEMS

FIELD

The present disclosure relates generally to interrogation and detection systems for radio-frequency (RF) tags, and more particularly, detection and inventory systems for potentially retained surgical items within surgical sites.

BACKGROUND

It is often useful to determine whether objects associated with a surgery are present in a patient's body before completion of the surgery. Such objects may take a variety of forms. For example, the objects may take the form of instruments, for instance, scalpels, scissors, forceps, hemostats, and/or clamps. Also, for example, the objects may take the form of related accessories and/or disposable objects, for instance, surgical sponges, gauzes, and/or pads. Failure to locate an object before closing the patient may require additional surgery, and in some instances, may have unintended medical consequences.

Accordingly, there is a need for a technology that is capable of providing both presence detection and tagged surgical item/implement identification functionality in the medical setting, as well as inventory controls of the tagged items/implements. Specifically, detecting the presence of, identifying, and maintaining inventory of tagged surgical items and materials that are used during the execution of a medical procedure. Technologies exist that enable these functions both individually as well as in conjunction with each other, but the methods and packaging of the discrete solutions used are not ideal for the application. More specifically, the components attached or affixed to the items being tracked are either too large physically and present nuisances or obstacles in the execution of the procedure, or the detection and identification performance of the solution may degrade rapidly in the presence of variable and uncontrolled dielectric or conductive materials.

Accordingly, there are needs for improvements in presence detection, tagged item identification, and inventory functionality in the medical setting.

SUMMARY

This disclosure relates to systems for detection of surgical objects and/or devices used in body cavities during surgery, specifically systems that include a dual detection tag attached to the surgical item and/or devices and an antenna to be placed directly next to a surgical site to detect and track such surgical objects and/or devices.

In accordance with aspects of the disclosure, an inventory system configured for detecting and counting potentially retained surgical items within a body of a patient includes a dual detection tag, a signal generator, and an antenna operably coupled to the signal generator. The dual detection tag includes a beacon tag configured to transmit a first return signal at a first frequency when energized and an RFID tag affixed configured to transmit a second return signal at a second frequency when energized. The signal generator is configured to generate an energizing signal for the beacon tag and/or the RFID tag. The antenna is configured to receive the first return signal transmitted by the beacon tag and/or the second return signal transmitted by the RFID tag.

In an aspect of the present disclosure, the first frequency may be a lower frequency than the second frequency.

In another aspect of the present disclosure, the RFID tag may include a substrate including polyimide, polyethylene terephthalate, polyethylene naphthalate, and/or polyester.

In yet another aspect of the present disclosure, the RFID tag may include a flexible substrate.

In a further aspect of the present disclosure, the RFID tag may be disposed around the beacon tag.

In yet a further aspect of the present disclosure, the dual detection tag may be affixed to a surgical item.

In an aspect of the present disclosure, the dual detection tag further may include a fabric pouch affixed to the surgical item.

In yet another aspect of the present disclosure, the system may further include a processor and a memory. The memory includes instructions stored thereon, which, when executed by the processor, may cause the system to energize the beacon tag and receive the first return signal from the antenna. The first return signal includes a first unique identifier.

In a further aspect of the present disclosure, the instructions, when executed by the processor, may further cause the system to energize the RFID tag and receive the second return signal from the antenna. The second return signal includes a data block.

In yet a further aspect of the present disclosure, the instructions, when executed by the processor, further cause the system to encrypt the data block, which contains the unique identifier of the dual detection tag.

In an aspect of the present disclosure, a dual detection tag includes a beacon tag configured to transmit a first return signal in response to a first energizing signal and an RFID tag configured to transmit a second return signal in response to a second energizing signal.

In accordance with aspects of the disclosure, the first return signal may include a first frequency when energized, and the second return signal may include a second frequency when energized.

In another aspect of the present disclosure, the first frequency may be a lower frequency than the second frequency.

In yet another aspect of the present disclosure, the beacon tag may include a cylindrical shape.

In a further aspect of the present disclosure, the dual detection tag may be contained within a pouch.

In yet a further aspect of the present disclosure, the pouch may include a material having transparency to electromagnetic frequency emissions.

In an aspect of the present disclosure, the pouch may be coupled to a surgical instrument.

In accordance with aspects of the disclosure, the dual detection tag may be coupled to a surgical instrument.

In yet a further aspect of the present disclosure, the dual detection tag may be coupled to gauze, surgical sponge, and/or padding.

In an aspect of the present disclosure, the RFID tag may be affixed around an outer face of the beacon tag.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements and have been solely selected for ease of recognition in the drawings.

Various aspects of the presently disclosed antennae, RF tags, and articles containing them are described herein below with reference to the drawings.

DETAILED DESCRIPTION

In the following description, certain specific details are set forth in order to provide a thorough understanding of disclosed aspects. However, one skilled in the relevant art will recognize that aspects may be practiced without one or more of these specific details or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

Figure 1:
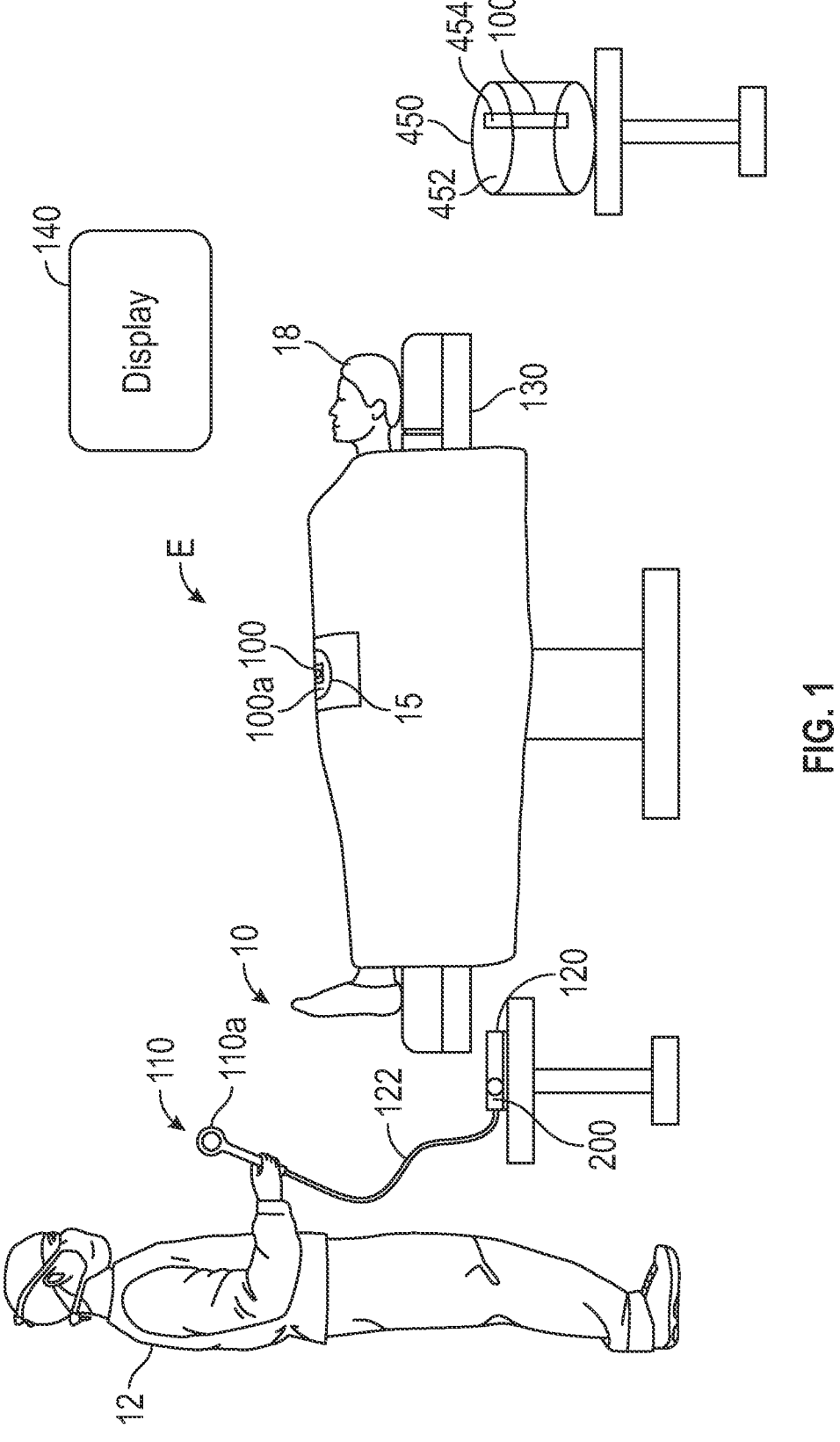
FIG. 1 is a schematic diagram showing a surgical environment illustrating a medical provider using an inventory system for detecting and counting an object within a patient that is tagged with an RFID tag according to one illustrated aspect.

FIG. 1 depicts a surgical environment "E" in which a medical provider 12 operates an inventory system 10 for detection and counting of beacon tags and radio-frequency identification (RFID) tags to ascertain the presence or absence of items, implements, or objects 100a in a patient 18. The inventory system 10 may include a signal generator 120 and an antenna 110 coupled to the signal generator 120 by one or more communication paths, for example, coaxial cable 122. In one aspect of the inventory system 10, the antenna 110 may take the form of a hand-held wand 110a.

The object 100a may take a variety of forms, for example, instruments, accessories, and/or disposable objects useful in performing surgical procedures. For instance, the object 100a may take the form of scalpels, scissors, forceps, hemostats, and/or clamps. Also, for example, the objects 100a may take the form of surgical sponges, gauze, and/or padding. The object 100a is tagged, carrying, attached, or otherwise coupled to an RFID tag 100.

In use, the medical provider 12 may position the wand 110a approximate the patient 18 in order to detect the presence or absence of the one or more dual detection tags 100 and hence an object 100a. The medical provider 12 may, in some aspects, move the wand 110a along and/or across the body of the patient 18. For a detailed description of an exemplary inventory system, reference may be made to commonly owned U.S. Patent Application Publication No. 2004/0250819 to Blair et al., entitled "Apparatus and Method for Detecting Objects Using Tags and Wideband Detection Device," filed Mar. 29, 2004, the entire contents of which is hereby incorporated by reference herein.

In aspects, the system 10 may include a display 140. The display may be used, for example, to display an inventory of potentially retained surgical items.

Figure 2:
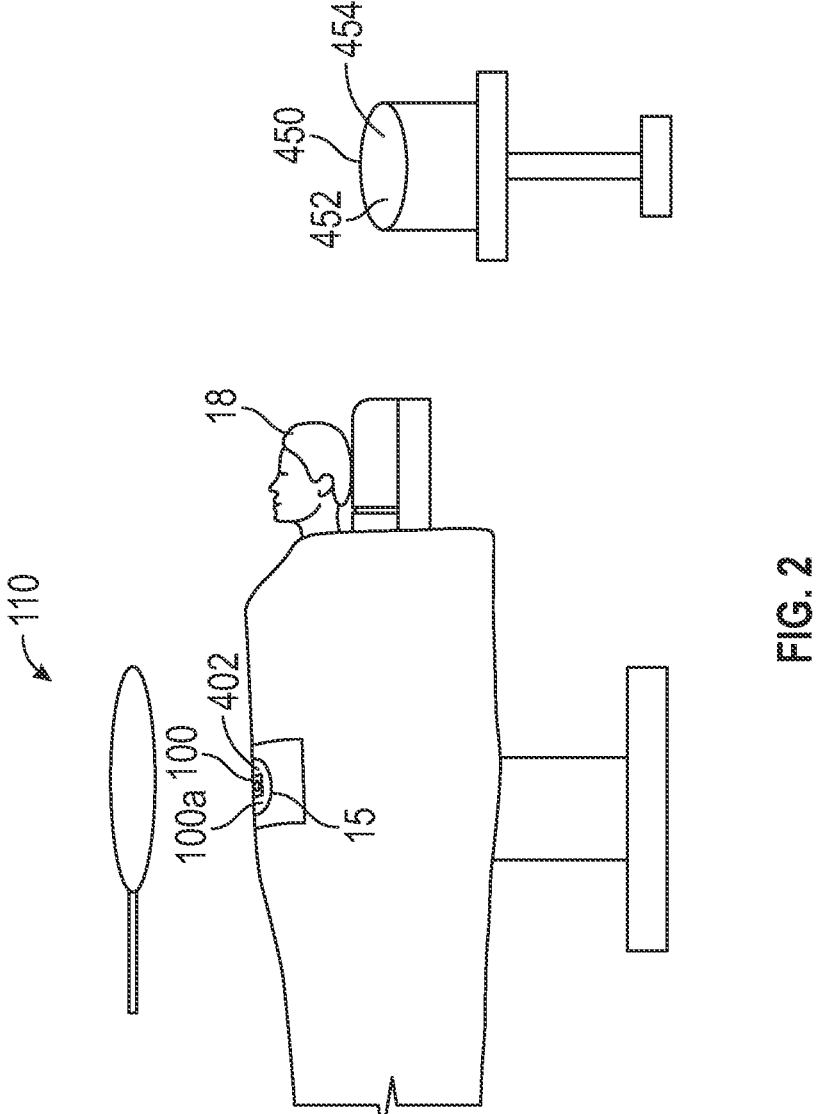
FIG. 2 is a schematic illustration of an antenna for detection of surgical implements within a patient's body in active use within a surgical site.

Referring now to FIG. 2, inventory system 10, for detection and counting of surgical implements (e.g., object 100a) within a patient's body, includes a signal generator 120 to provide an energizing signal for one or more dual detection tags 100 (FIG. 1) affixed to an object 100a (FIG. 1). Each RFID tag 100 is configured to transmit a return signal when energized, such that an antenna 110 can detect the return signal and confirm the presence of objects 100a within the body of patient 18. The antenna 110 is operably coupled to the signal generator 120 via a communication cable 122, which may be of variable length to provide greater range of motion to the clinician handling the antenna 110. The signal generator 120 may include a controller 200.

In one aspect of inventory system 10, the antenna 110 is an antenna 110 configured to be waved over the surgical site 15, e.g., over the body of patient 18. For example, the antenna 110 may be held over the body of the patient 18 at the height of about four or about five inches while attempting to detect dual detection tags 100 (e.g., beacon tags 500 and/or RFID tags 600), so that the user may detect and/or confirm the presence of objects 100a within the body of patient 18.

The system 10 may further include an RFID-enabled secure package 450 (e.g., RFID-enabled smart packaging and/or RFID enabled secure mutual authentication packaging) which includes an RFID tag affixed thereto. For example, an RFID tag may be secured to a lid or a body of the RFID-enabled secure package 450. The beacon tag 500 is configured to transmit a first return signal when energized. Generally, the RFID-enabled secure package 450 will include a surgical item 454 (e.g., cotton swabs) configured to be removed from the RFID-enabled secure package 450. The surgical item 454 includes a retained surgical item RFID tag, e.g., the dual detection tag 100, affixed to the surgical item 454. The surgical item 454 may include, for example, any surgical sponge, cotton swab, instrument, tool, and/or device that is unintentionally left in the patient at the completion of a surgery or other procedure. The RFID tag 500 is configured to transmit a second return signal when energized.

The RFID-enabled secure package 450 includes, but is not limited to, for example, caps and closures and are generally configured to verify the contents of sealed containers to ensure the product is genuine, not part of a recall, within the expiration date, and/or has not been tampered with or diverted. RFID-enabled secure package 450 generally includes a secure package RFID tag 452.

In aspects, the retained surgical item dual detection tag 100 may be linked to the secure package RFID tag 452 by embedding an encrypted block of data that contains the unique identifier of the RFID tag 600. For example, to enable the use of the retained surgical items 454, the RFID tag 600 may be scanned by the antenna 110 in the inventory system 10.

Figure 3:
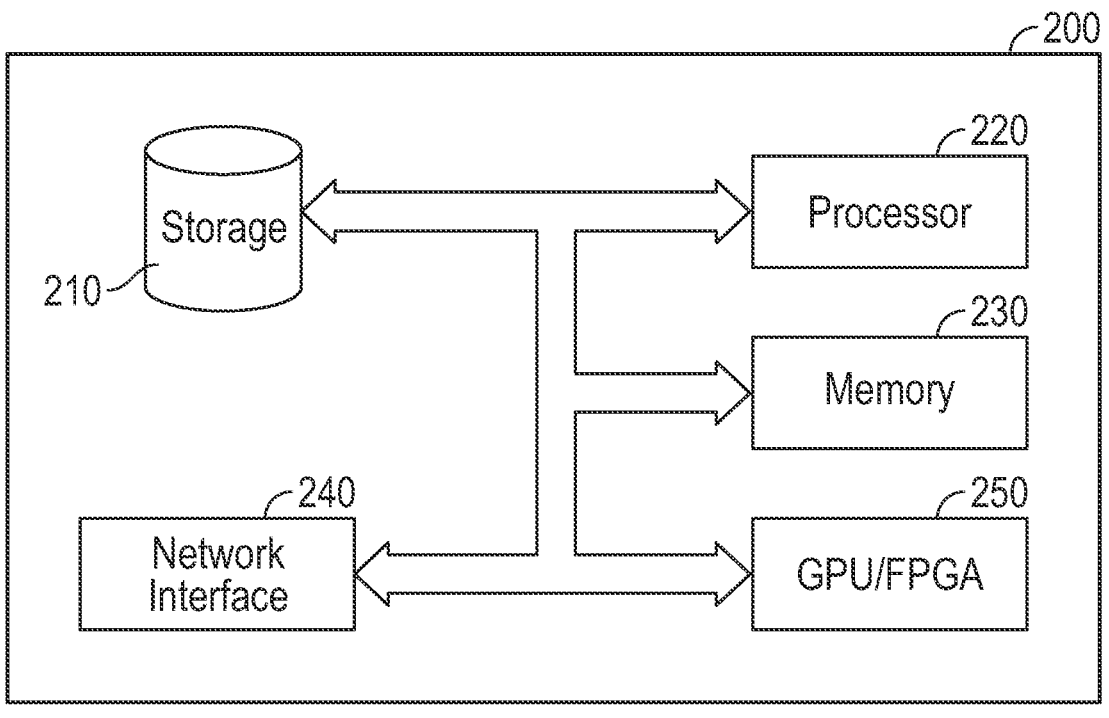
FIG. 3 is a block diagram of a controller of the system of FIG. 1.

FIG. 3 illustrates that controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as, without limitation, a digital signal processor, a microprocessor, an ASIC, a graphics processing unit (GPU), a field-program-mable gate array (FPGA), or a central processing unit (CPU). In certain aspects of the disclosure, network infer-ence may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communi-nication buses of a circuit board and/or through communi-cation cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data.

Figure 4:
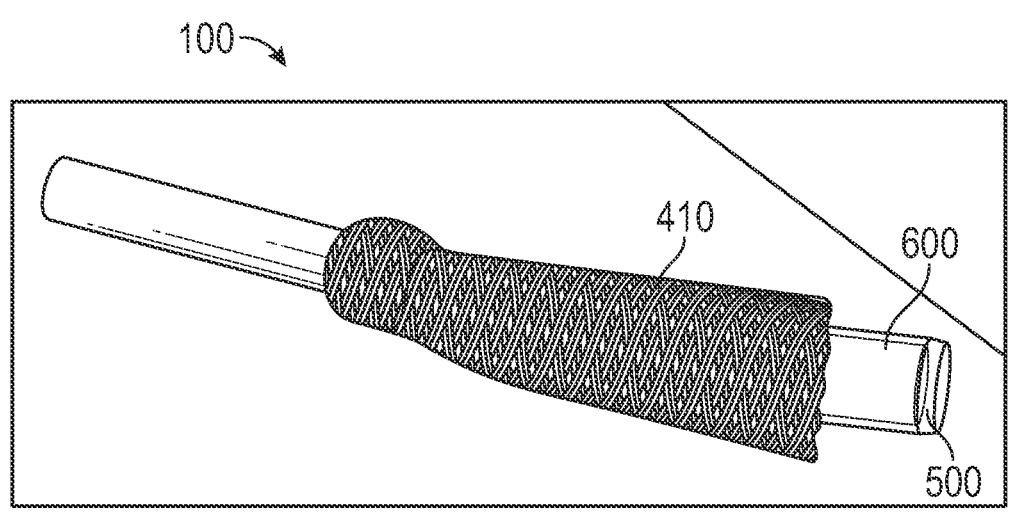
FIG. 4 is a diagram of the dual detection tag of the system of FIG. 1.

Referring to FIG. 4, there is shown the dual detection tag 100 of the system of FIG. 1. The dual detection tag 100 generally includes a beacon tag 500 configured to transmit a first return signal at a first frequency when energized and a RFID tag 600 affixed to the beacon tag 500.

The RFID tag 600 is configured to transmit a second return signal at a second frequency when energized. The first frequency is a lower frequency than the second frequency. For example, the first frequency may be in the range of about 30 kHz to about 300 kHz and the second frequency may be in the range of about 300 MHz to about 3 GHz. A benefit of the dual detection tag 100 is that it has a small size (e.g., about 12 mm long to about 23 mm long and about 3 mm to about 7 mm in diameter), which is desirable to the clinician such that the size does not interfere with the use of a surgical gauze and/or sponge.

The RFID tag 600 may be disposed around the beacon tag 500. The dual detection tag 100 may include a pouch 410 (e.g., a sleeve) made from a biocompatible material (for example, fabric such as cotton and/or polyester), which is configured to hold the beacon tag 500 and the RFID tag 600. The pouch 410 may be made of a braided material. In aspects, the pouch is made of a material that is transparent to electromagnetic frequency emissions so as to not block the signals going to and from the beacon tag 500 and the RFID tag 600.

Figure 5:
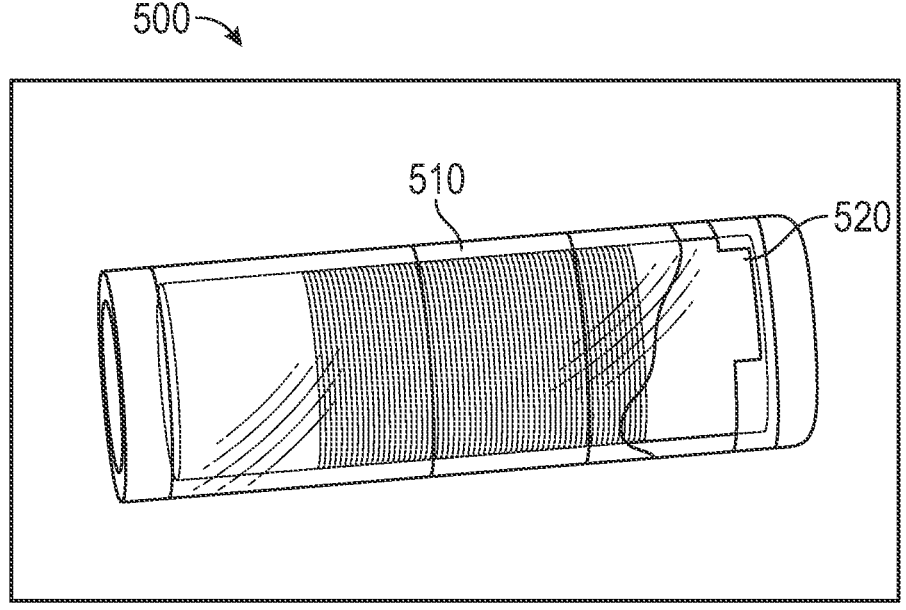
FIG. 5 is a diagram of a cylindrical beacon tag of the dual detection tag of FIG. 4.

Referring to FIG. 5, the beacon tag 500 is shown. The beacon tag 500 may be an L-C (inductor-capacitor) resonant tag, such as, for example, a tag having the first frequency range of about 30 kHz to about 300 kHz described above. L-C tags typically have a read range of about 20 cm and generally have a better ability to be transmitted and received in all directions. The beacon tag 500 may be used to count and/or identify items inside of a patient 18 (FIG. 1). The beacon tag 500 may include a cylindrical shape.

Figure 6:
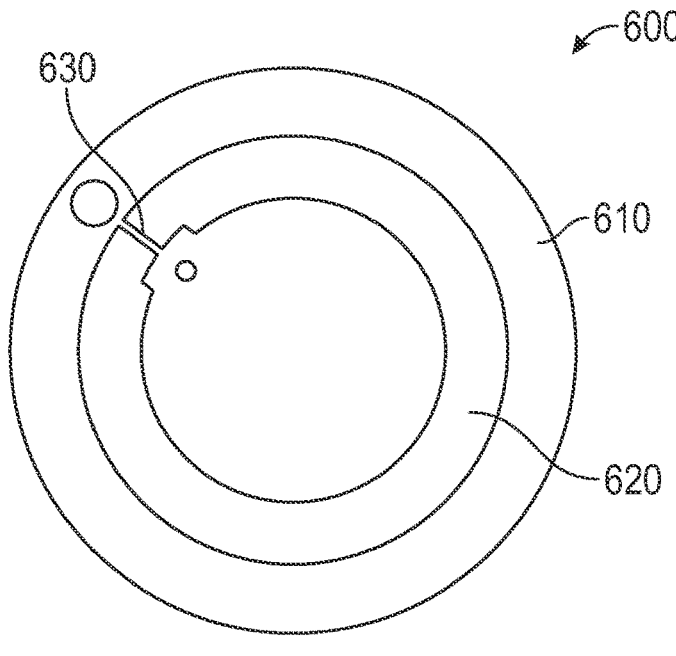
FIG. 6 is a diagram of a thin film UHF RFID tag of the dual detection tag of FIG. 4.

Referring to FIG. 6, the RFID tag 600 is shown. The RFID tag 600 generally includes a substrate 610, an antenna 620 disposed on the substrate 610, and a transceiver circuit 630 operably connected to the antenna 620. The transceiver circuit 630 is configured to transmit and receive RF signals. The RFID tag 600 may be an ultra-high frequency (UHF) RFID tag, such as, for example, a tag having a frequency range of about 300 MHz to about 3 GHz described above. UHF RFID tags typically have a read range of about 12 meters. The RFID tag 600 may be used to count and/or identify items outside of a patient 18 (FIG. 1). The RFID tag 600 may include a flexible substrate 610 (FIG. 6), such as, for example, polyimide, polyethylene terephthalate, poly-ethylene naphthalate, and/or polyester. The RFID tag 600 may be a thin film UHF RFID tag.

Figure 7:
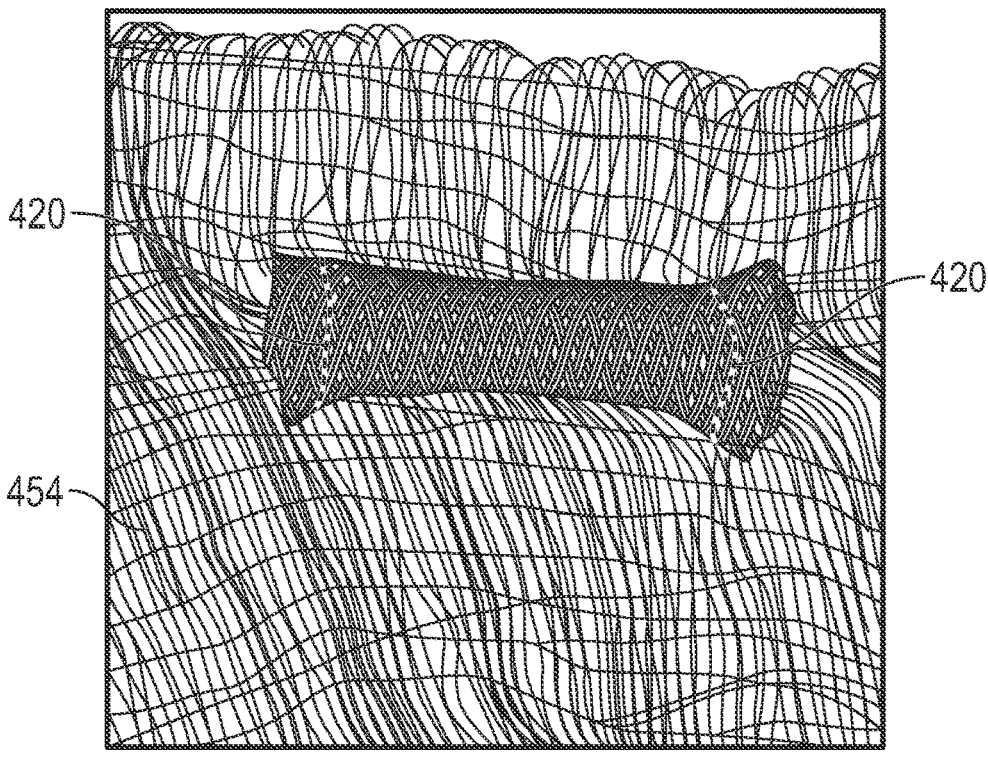
FIG. 7 is a diagram of the dual detection tag of FIG. 4 attached to a surgical gauze.
Figure 8:
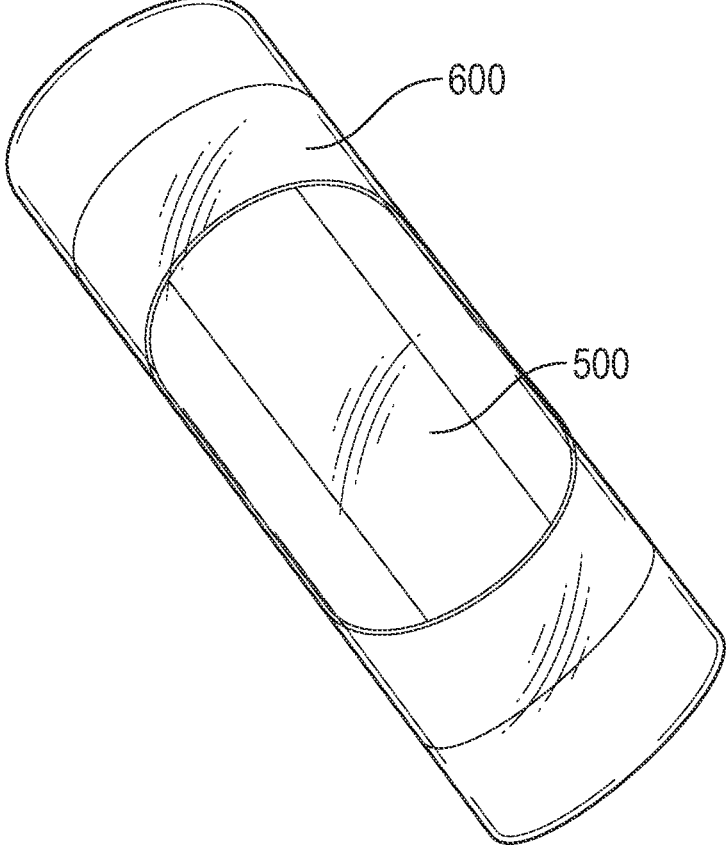
FIG. 8 is a diagram of the thin film UHF RFID tag of FIG. 6 wrapped around the cylindrical beacon tag of FIG. 5.

Referring to FIG. 7, the dual detection tag 100 may be attached to a surgical item 454 (e.g., surgical gauze and/or a surgical sponge). For example, the pouch 410 of the dual detection tag 100 may be stitched 420 to the surgical item 454, or attached using other suitable methods (e.g., adhe-sive).

The two main functions of an inventory system 10 (such as an operating room safety system) are to detect and count potentially retained surgical items (RSIs). The term retained surgical item, as used herein, includes any surgical sponge, instrument, tool, and/or device that is unintentionally left in the patient at the completion of a surgery or other procedure. The disclosed technology detects and counts potential RSIs, each of which includes an RFID, in a secure fashion and in a way that provides individual identification to each RFID based potential retained surgical item.

A benefit of the disclosed technology is that it does not require that the RFID tag 600 have the capability to perform a cryptographic function such as mutual authentication to assess authenticity. For example, the RFID tag 600 of a potential RSI 454 may have limited memory space due to size, cost, or performance constraints yet could still be used in this system.

In aspects, the system may include an RFID-enabled secure package 450 (e.g., smart packaging), which includes a set of manufactured potential RSIs 454 (such as cotton sponges). The RFID-enabled secure package 450 includes an RFID tag 452 (e.g., an RFID chip), which is capable of mutual authentication with a host (e.g., controller 200).

A method of use of the system 10 and dual detection tag 100, in accordance with the present disclosure, is presented below. Initially, the signal generator 120, of the system 10, generates an energizing signal and energizes the dual detec-tion tag 100, which is affixed to a surgical item 454 (e.g., surgical gauze).

Next, the controller 200 of the system 10 receives a return signal from the antenna 110 (FIG. 1). In aspects, the return signal may include a unique identifier. The unique identifier may include, for example, an identification code uniquely identifying the RFID tag 452 of the RFID-enabled secure package 450 (FIG. 1).

In aspects, the beacon tag 500 (or RFID tag 600) of the dual detection tag 100 may be programmed with unique derived keys based on a unique identifier. In cryptography, a derived unique key is a key management scheme in which for every transaction, a unique key is used which is derived from a fixed key. A key is a string of characters used within an encryption algorithm for altering data so that it appears random. A key locks (encrypts) data so that only a user with the right key can unlock (decrypt) the encrypted data.

Next, the controller 200 generates a key based on the unique identifier. The key may include a symmetric or asymmetric key. Symmetric encryption uses mathematical permutations to encrypt a plain text message. It also uses the same mathematical permutation, known as a key, to decrypt messages. Asymmetric encryption also uses mathematical permutations to encrypt a plain text message, but it uses two different permutations, still known as keys, to encrypt and decrypt messages. With asymmetric cryptography, a public key that can be shared with anyone gets used to encrypt messages while a private key that is known only by the recipient gets used to decrypt messages.

In aspects, the signal generator 120 may energize the RFID tag 600 of the dual detection tag 100 using the generated energizing signal. The RFID tag 600 is configured to transmit a second return signal when energized. For example, the RSI data block may be as small as 128 bits in the case of Advanced Encryption Standard (AES) encryption in the LF RFID tag, and/or for the UHF RFID chip/tag. In aspects, the derived key may also be based on, for example, a random identifier (RID) and/or a non-unique identifier (NUID).

Next, the controller 200 receives the second return signal from the antenna 110. The return signal includes a data block. For example, the beacon tag 500 and/or the RFID tag 600 may include 1K of data. The data may be organized into sixteen sectors, and each sector may be organized into about four data blocks. Each block of data may store sixteen bytes of data.

Next, the controller 200 may decrypt the data-block based on the key and determines if the decrypted data-block includes the unique identifier. For example, the decrypted data block may include the 7 bit UID.

In aspects, controller 200 may display, on a display 140, an inventory of potentially retained surgical items. For example, the system 10 may display the total number of surgical items and their status (e.g., retained and/or accounted for) and may provide an alert if any potentially retained surgical items are not accounted for.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting but merely as exemplifications of particular aspects. Those skilled in the art will envision other modifications within the scope of the claims appended hereto.

What is claimed is:

1. An inventory system configured for detecting and counting potentially retained surgical items within a body of a patient, the inventory system comprising:
   a surgical item;
   a dual detection tag affixed to the surgical item, the dual detection tag including:
      a beacon tag configured to transmit a first return signal at a first frequency when energized, the beacon tag cylindrically shaped; and
      a RFID tag configured to transmit a second return signal at a second frequency when energized, wherein the RFID tag surrounds an outer face of the beacon tag;
   a signal generator configured to generate an energizing signal for at least one of the beacon tag or the RFID tag; and an antenna operably coupled to the signal generator, the antenna configured to receive at least one of the first return signal transmitted by at least one of the beacon tag or the second return signal transmitted by the RFID tag.

2. The system of claim 1, wherein the first frequency is a lower frequency than the second frequency.

3. The system of claim 1, wherein the RFID tag includes a substrate including at least one of polyimide, polyethylene terephthalate, polyethylene naphtholate, or polyester.

4. The system of claim 1, wherein the RFID tag includes a flexible substrate.

5. The system of claim 1 wherein the dual detection tag is affixed to a surgical item.

6. The system of claim 5, wherein the dual detection tag further includes a fabric pouch affixed to the surgical item.

7. The system of claim 1, wherein the system further includes:
   a processor; and
   a memory, including instructions stored thereon, which when executed by the processor cause the system to:
      energize the beacon tag, by the energizing signal; and
      receive the first return signal from the antenna, the first return signal including a first unique identifier.

8. The system of claim 7, wherein the instructions, when executed by the processor, further cause the system to:
   energize the RFID tag; and
   receive the second return signal from the antenna, the second return signal including a data-block.

9. The system of claim 8, wherein the instructions, when executed by the processor, further cause the system to encrypt the data-block which contains the unique identifier of the beacon tag.

10. A dual detection tag apparatus comprising:
   a surgical item,
   a beacon tag configured to transmit a first return signal in response to a first energizing signal, wherein the beacon tag is cylindrical; and
   a RFID tag configured to transmit a second return signal in response to a second energizing signal, wherein the RFID tag surrounds an outer face of the beacon tag,
   wherein the dual detection tag is attached to the surgical item.

11. The dual detection tag of claim 10, wherein the first return signal includes a first frequency when energized, and the second return signal includes a second frequency when energized.

12. The dual detection tag of claim 11, wherein the first frequency is a lower frequency than the second frequency.

13. The dual detection tag of claim 10, wherein the beacon tag includes a cylindrical shape.

14. The dual detection tag of claim 10, wherein the dual detection tag is contained within a pouch.

15. The dual detection tag of claim 14, wherein the pouch includes a material having transparency to electromagnetic frequency emissions.

16. The dual detection tag of claim 14, wherein the pouch is coupled to a surgical instrument.

17. The dual detection tag of claim 10, wherein the dual detection tag is coupled to a surgical instrument.

18. The dual detection tag of claim 10, wherein the dual detection tag is coupled to at least one of gauze, surgical sponge, or padding.

* * * * *